United States Patent
Cheung

(10) Patent No.: US 6,649,383 B1
(45) Date of Patent: Nov. 18, 2003

(54) DIETARY SUPPLEMENTS BENEFICIAL FOR THE GASTROINTESTINAL SYSTEM

(75) Inventor: Ling Yuk Cheung, New Territories (HK)

(73) Assignee: Ultra Biotech Limited, Douglas (GB)

(*) Notice: Subject to any disclaimer, the term of this patent is extended or adjusted under 35 U.S.C. 154(b) by 0 days.

(21) Appl. No.: 10/187,140

(22) Filed: Jun. 28, 2002

(51) Int. Cl.$^7$ .......................... C12N 13/00; C12N 1/00; C12N 1/14

(52) U.S. Cl. ................. 435/173.1; 435/243; 435/254.1; 435/255.2; 435/255.21; 435/940

(58) Field of Search .......................... 435/173.1, 243, 435/254.1, 255.2, 255.21, 940

(56) References Cited

U.S. PATENT DOCUMENTS

| | | | |
|---|---|---|---|
| 4,081,367 A | 3/1978 | Hulls et al. | 210/610 |
| 4,183,807 A | 1/1980 | Yoshizawa et al. | 210/611 |
| 4,211,645 A | 7/1980 | Zajic et al. | 210/611 |
| 4,559,305 A | 12/1985 | Zajic et al. | 435/243 |
| 4,816,158 A | 3/1989 | Shimura et al. | 210/610 |
| 5,075,008 A | 12/1991 | Chigusa et al. | 210/610 |
| 5,106,594 A | 4/1992 | Held et al. | 422/292 |
| 5,416,010 A | 5/1995 | Langenberg et al. | 435/468 |
| 5,476,787 A | 12/1995 | Yokoyama et al. | 435/262.5 |
| 5,567,314 A | 10/1996 | Chigusa et al. | 210/150 |
| 5,578,486 A | 11/1996 | Zhang | 435/243 |
| 5,707,524 A | 1/1998 | Potter | 210/606 |
| 5,879,928 A | 3/1999 | Dale et al. | 435/264 |
| 6,036,854 A | 3/2000 | Potter | 210/177 |
| 6,391,617 B1 | 5/2002 | Cheung | 435/254 |
| 6,391,618 B1 | 5/2002 | Cheung | 435/255 |
| 6,391,619 B1 | 5/2002 | Cheung | 435/255 |
| 6,436,695 B1 | 8/2002 | Cheung | 435/254 |
| 6,440,713 B1 | 8/2002 | Cheung | 435/173 |
| 2002/0123127 A1 | 9/2002 | Cheung | 435/254.21 |
| 2002/0123129 A1 | 9/2002 | Cheung | 435/254.21 |
| 2002/0123130 A1 | 9/2002 | Cheung | 435/262.5 |

FOREIGN PATENT DOCUMENTS

| | | |
|---|---|---|
| CN | 1110317 A | 10/1995 |
| EP | 0041373 | 12/1981 |
| FR | 2222433 | 10/1974 |
| JP | 60028893 | 2/1985 |
| RU | 415983 A | 11/1974 |
| RU | 1071637 | 2/1984 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/070682 A2 | 9/2002 |

OTHER PUBLICATIONS

K. Asami et al., "Real–Time Monitoring of Yeast Cell Division by Dielectric Spectroscopy", *Biophysical Journal*, 76, pp. 3345–3348 (1999).

E.K. Balcer–Kubiczek et al., "Expression Analysis of Human HL60 Cells Exposed to 60 Hz Square–or Sine–Wave Magnetic Fields", *Radiation Research*, 153, pp. 670–678 (2000).

C.A.L. Basset et al., "Beneficial Effects of Electromagnetic Fields", *Journal of Cellular Biochemistry*, 51, pp. 387–393 (1993).

P. Conti et al., "Effect of Electromagnetic Fields on Several CD Markers and Transcription and Expression of CD4", *Immunobiology*, 201, pp. 36–48 (1999).

A.M. Gonzalez et al., "Effects of an Electric Field of Sinusoidal Waves on the Amino Acid Biosynthesis by Azotobacter", *Z. Naturforsch*, 35, pp. 258–261 (1980).

E.M. Goodman et al., "Effects of Electromagnetic Fields on Molecules and Cells", *International Review of Cytology*, 158, pp. 279–339 (1995).

T. Grospietsch et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

W. Grundler et al., "Nonthermal Effects of Millimeter Microwave on Yeast Growth", *Z. Naturforsch*, 33, pp. 15–22 (1978).

W. Grundler et al., "Mechanisms of Electromagnetic Interaction with Cellular Systems", *Naturwissenschaften*, 79, pp. 551–559 (1992).

O.I. Ivaschuk et al., "Exposure of Nerve Growth Factor–Treated PC12 Rat Pheochromocytoma Cells to a Modulated Radiofrequency Field at 836.55 MHz: Effects on c–jun and c–fos Expression", *Bioelectromagnetics*, 18, pp. 223–229 (1997).

F. Jelinek et al., "Microelectronic Sensors for Measurement of Electromagnetic Fields of Living Cells and Experimental Results", *Bioelectrochemistry and Bioenergetics*, 48, pp. 261–266 (1999).

A. Lacy–Hulbert et al., "Biological Responses to Electromagnetic Fields", *FASEB Journal*, 12, pp. 395–420 (1998).

C.R. Libertin et al., "Effects of Gamma Rays, Ultraviolet Radiation, Sunlight, Microwave and Electromagnetic Fields on Gene Expression Mediated by Human Immunodeficiency Virus Promoter", *Radiation Research*, 140, pp. 91–96 (1994).

H. Lin et al., "Specific Region of the c–myc Promoter Is Responsive to Electric and Magnetic Fields", *Journal of Cellular Biochemistry*, 54, pp. 281–288 (1994).

(List continued on next page.)

Primary Examiner—Christopher R. Tate
Assistant Examiner—Randall Winston
(74) Attorney, Agent, or Firm—Fish & Neave; James F. Haley, Jr.; Z. Ying Li

(57) ABSTRACT

Compositions comprising a plurality of yeast cells, wherein said plurality of yeast cells are characterized by their ability to increase secretion of gastric juice or alleviate gastric ulcer in a mammal, said ability resulting from their having been cultured in the presence of an alternating electric field having a specific frequency and a specific field strength. Also included are methods of making and using these compositions.

9 Claims, 2 Drawing Sheets

OTHER PUBLICATIONS

H. Lin et al., "Magnetic Field Activation of Protein–DNA Binding", *Journal of Cellular Biochemistry*, 70, pp. 297–303 (1998).

L.I. Loberg et al., "Expression of Cancer–Related Genes in Human Cells Exposed to 60 Hz Magnetic Fields", *Radiation Research*, 153, pp. 679–684 (2000).

R.L. Moore, "Biological Effects of Magnetic Fields: Studies with Microorganisms", *Canadian Journal of Microbiology*, 25, pp. 1145–1151 (1979).

C.A. Morehouse et al., "Exposure of Daudi Cells to Low–Frequency Magnetic Fields Does Not Elevate MYC Steady–State mRNA Levels", *Radiation Research*, 153, pp. 663–669 (2000).

V. Norris et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

G. Novelli et al., "Study of the Effects of DNA of Electromagnetic Fields Using Clamped Homogeneous Electric Field Gel Electrophoresis", *Biomedicine & Pharmacotherapy*, 45, pp. 451–454 (1991).

J.L. Phillips, "Effects of Electromagnetic Field Exposure on Gene Transcription", *Journal of Cellular Biochemistry*, 51, pp. 381–386 (1993).

V. Romano–Spica et al., "Ets1 Oncogene Induction by ELF–Modulated 50 MHz Radiofrequency Electromagnetic Field", *Bioelectromagnetics*, 21, pp. 8–18 (2000).

J.E. Trosko, "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

C. Ventura et al., "Elf–pulsed Magnetic Fields Modulate Opioid Peptide Gene Expression in Myocardial Cells", *Cardiovascular Research*, 45, pp. 1054–1064 (2000).

A.M. Woodward et al., "Genetic Programming as an Analytical Tool for Non–linear Dielectric Spectroscopy", *Bioelectrochemistry and Bioenergetics*, 48, pp. 389–396 (1999).

T. Yonetani et al., "Electromagnetic Properties of Hemoproteins", *The Journal of Biological Chemistry*, 247, pp. 2447–2455 (1972).

L. Zhang et al., "Electrostimulation of the Dehydrogenase System of Yeast by Alternating Currents", *Bioelectrochemistry and Bioenergetics*, 28, pp. 341–353 (1992).

Binninger, D. M. et al., "Effects of 60Hz AC magnetic fields on gene expression following exposure over multiple cell generations using *Saccharomyces cerevisiae*", *Bioelectrochemistry and Bioenergetics*, 43(1):83–89 (1997).

Deguchi, T. et al., "Nylon biodegradation by lignin–degrading fungi", *Applied and Environmental Microbiology*, 63(1):329–331 (1997).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material–relation to food processing", *Radiation Physics and Chemistry*, 45(4): 591–607 (1995).

Van Rensburg, P. et al., "Engineering yeast for efficient cellulose degradation", *Yeast*, 14(1): 67–76 (1998).

"*Saccharomyces cerevisiae* Meyen ex Hansen", China Catalogue of Cultures/China Committee of Culture Collection for Microorganisms (CCCCM), "www.im.ac.cn/database/YEAST/y122.htm", Apr. 24, 1996, retrieved on Nov. 27, 2002.

DIETARY SUPPLEMENTS BENEFICIAL FOR THE GASTROINTESTINAL SYSTEM

FIELD OF THE INVENTION

The invention relates to compositions that are beneficial for the gastrointestinal system and useful as a dietary supplement. These compositions contain yeast cells obtainable by growth in electromagnetic fields with specific frequencies and field strengths.

BACKGROUND OF THE INVENTION

Gastric discomfort is a common ailment. In a healthy human stomach and duodenum, an effective balance exists between the potential for gastric acid and pepsin to damage gastric mucosal cells, and the ability of these gastric mucosal cells to protect themselves from injury. Disruption of this balance has been attributed to several factors, including environmental and emotional stress, age, diet, genetics and individual behavior. This disruption is evidenced as a burning, aching or gnawing pain that may be perceived as abdominal pressure or fullness. Most of the symptoms experienced by patients under such conditions result from a breakdown of the normal mucosal defense mechanisms. Various studies have demonstrated that gastric acid and pepsin are important in the pathogenesis of dyspepsia, stomach upset, gastroesophageal reflux disease, and duodenal and gastric ulcer.

Several mechanisms are believed to be important in protecting gastric and duodenal mucosa from damage by gastric acid, pepsin, bile pancreatic enzymes, as well as external stress factors. These defense mechanisms include mucus, mucosal blood flow, cell renewal and bicarbonate. These factors acting in balance help maintain mucosal integrity.

Physical stress has been shown to induce significant gastrointestinal mucosal injury in animals. Water-immersion restraint stress of rats results in an increase in cell loss accompanied by an accelerated cell migration and macroscopic mucosal injury. Cell migration was found to be accelerated in fandic mucosa after 90 minutes of exposure to stress. A combination of increased cell loss and depressed epithelial proliferation may play a role in stress-related gastric lesions and injury in the rats. It has been suggested that oxygen free radicals are greatly involved in the pathogenesis of gastric injury. Free radicals may play a major role in stress-induced gastrointestinal injury.

Current treatments for gastric discomfort include administration of antacids and $H_2$-receptor antagonists. However, these treatments are not effective in preventing stress-induced gastric injury or other gastrointestinal ailments over the long term. There remains a need for an effective method to treat gastrointestinal discomfort.

SUMMARY OF THE INVENTION

This invention is based on the discovery that certain yeast cells can be activated by electromagnetic fields having specific frequencies and field strengths to produce substances that are beneficial for the gastrointestinal system. Compositions comprising these activated yeast cells can be used as dietary supplement for improving gastrointestinal health, e.g., for alleviating gastritis, gastric ulcer, inadequate gastric acid secretion, indigestion and other gastrointestinal ailments.

This invention embraces a composition comprising a plurality of yeast cells that have been cultured in an alternating electric field having a frequency in the range of about 18000–18200 MHz (e.g., 18100–18150 MHz), and a field intensity in the range of about 100 to 420 mV/cm (e.g., 120–410 mV/cm). The yeast cells are cultured in the alternating electric field for a period of time sufficient to substantially increase the capability of said plurality of yeast cells to produce substances beneficial for the gastrointestinal system. For instance, the cultured yeast cells when ingested can increase (e.g., by at least 10% such as 20%, 50%, 100%, 200%, and 300%) the secretion of gastric acid and/or the activity level of pepsin, and/or alleviate (e.g., by at least 10% such as 20% and 100%) gastric ulcer in a mammal.

In one embodiment, the frequency and/or the field strength of the alternating electric field can be altered within the aforementioned ranges during said period of time. In other words, the yeast cells can be exposed to a series of electromagnetic fields. An exemplary period of time is about 40–120 hours (e.g., 60 to 98 hours).

Yeast cells that can be included in this composition can all be obtained from the China General Microbiological Culture Collection Center ("CGMCC"), a depository recognized under the Budapest Treaty (China Committee for Culture Collection of Microorganisms, Institute of Microbiology, Chinese Academy of Sciences, Haidian, P.O. BOX 2714, Beijing, 100080, China). Useful yeast species include, but are not limited to, *Saccharomyces cerevisiae, Saccharomyces carlsbergensis, Saccharomyces chevalieri, Saccharomyces delbrueckii, Saccharomyces exiguous, Saccharomyces fermentati, Saccharomyces logos, Saccharomyces mellis, Saccharomyces oviformis, Saccharomyces rosei, Saccharomyces rouxii, Saccharomyces sake, Saccharomyces uvarum, Saccharomyces willianus,* Saccharomyces sp., *Schizosaccharomyces octosporus, Schizosaccharomyces pombe, Sporobolomyces roseus, Torulopsis candida, Torulopsisfamta, Torulopsis globosa, Torulopsis inconspicua, Trichosporon behrendii, Trichosporon capitatum, Trichosporon cutaneum, Wickerhamia fluoresens, Candida arborea, Candida krusei, Candida lambica, Candida lipolytica, Candida parapsilosis, Candida pulcherrima, Candida rugousa, Candida tropicalis, Candida utilis, Crebrothecium ashbyii, Geotrichum candidum, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichia farinosa, Pichia membranaefaciens, Rhodosporidium toruloides, Rhodotorula glutinis, Rhodotorula minuta, Rhodotorula rubar, Rhodotorula aurantiaca, Saccharomycodes ludwigii,* and *Saccharomycodes sinenses.* For instance, the yeast cells can be of the strain *Saccharomyces cerevisiae* Hansen AS2.375, AS2.501, AS2.502, AS2.503, AS2.504, AS2.535, AS2.558, AS2.560, AS2.561, AS2.562 or IFFI1048; or *Saccharomyces carlsbergensis* Hansen AS2.420 or AS2.444.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising," will be understood to imply the inclusion of a stated integer or group of integers but not the exclusion of any other integer or group of integers.

Other features and advantages of the invention will be apparent from the following detailed description, and from the claims.

DETAILED DESCRIPTION OF THE INVENTION

Figure 1:
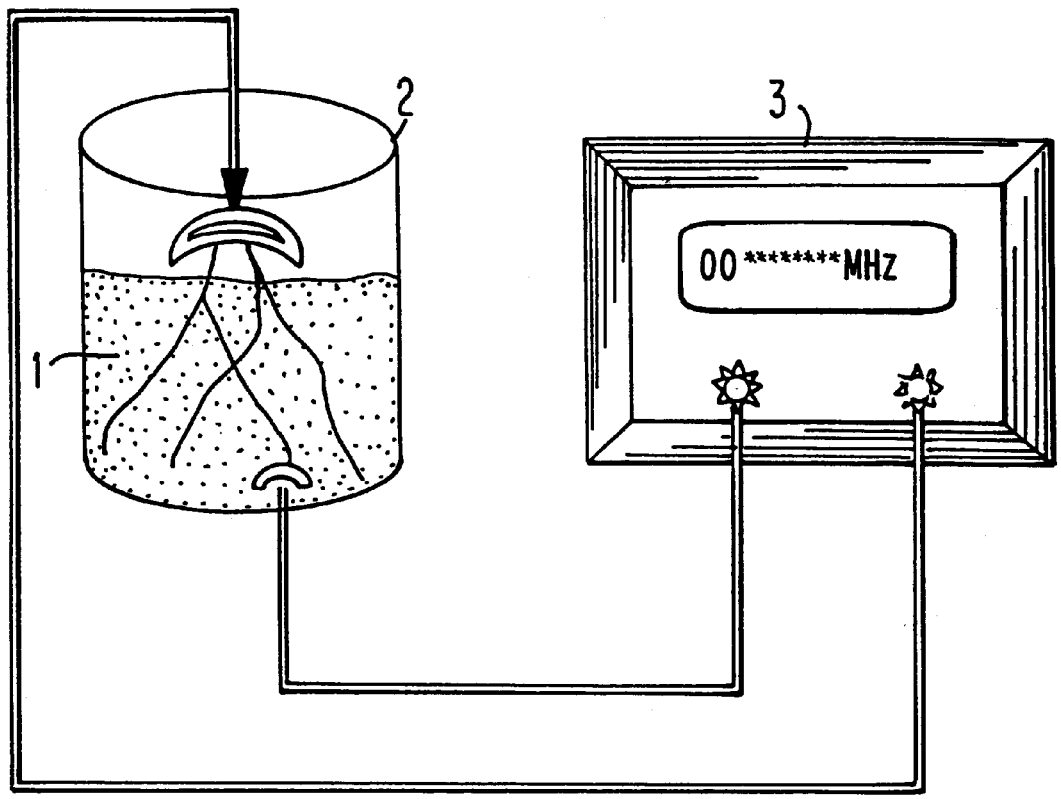
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("ENT") having specific frequencies and field strengths to produce agents useful in treating gastrointestinal ailments. Yeast compositions containing activated yeast cells can be used as a dietary supplement in the form of health drinks or dietary pills.

In certain embodiments, the yeast compositions of this invention stimulate the secretion of gastric acid. In other embodiments, the yeast compositions alleviate the symptoms of gastric ulcer. In further embodiments, the yeast compositions inhibit the growth of *Campylobacter pylori*, thereby mitigating gastric ulcer caused by the bacteria.

Since the activated yeast cells contained in these yeast compositions have been cultured to endure acidic conditions (pH 2.5–4.2), the compositions are stable in the stomach and can pass on to the intestines. Once in the intestines, the yeast cells are ruptured by various digestive enzymes, and the bioactive agents are released and readily absorbed.

Without being bound by any theory or mechanism, the inventor believes that EMFs activate or enhance the expression of a gene or a set of genes or alter the conformation and/or activity of certain cellular components (e.g. DNA, RNA, enzymes/proteins) in the yeast cells, resulting in the production of agents that are beneficial for the gastrointestinal system.

I. Yeast Strains Useful in the Invention

The types of yeasts useful in this invention include, but are not limited to, yeasts of the genera of Saccharomyces, Candida, Crebrothecium, Geotrichum, Hansenula, Kloeckera, Lipomyces, Pichia, Rhodosporidium, Rhodotorula, Saccharomycodes, Schizosaccharomyces, Sporobolomyces, Torulopsis, Trichosporon, and Wickerhamia.

Exemplary species within the above-listed genera include, but are not limited to, the species illustrated in Table 1. Yeast strains useful in this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with the accession numbers of CGMCC) are *Saccharomyces cerevisiae* Hansen AS2.375, AS2.501, AS2.502, AS2.503, AS2.504, AS2.535, AS2.558, AS2.560, AS2.561, AS2.562 and IFFI1048; and *Saccharomyces carlsbergensis* Hansen AS2.420 and AS2.444. Other non-limiting examples of useful strains are listed in Table 1. In general, yeast strains preferred in this invention are those used for fermentation in the food and wine industries. As a result, compositions containing these yeast cells are safe for human consumption.

Although it is preferred, the preparation of the yeast compositions of this invention is not limited to starting with a pure strain of yeast. A yeast composition of the invention may be produced by culturing a mixture of yeast cells of different species or strains.

TABLE 1

Exemplary Yeast Strains

*Saccharomyces cerevisiae* Hansen

| | | | | |
|---|---|---|---|---|
| ACCC2034 | ACCC2035 | ACCC2036 | ACCC2037 | ACCC2038 |
| ACCC2039 | ACCC2040 | ACCC2041 | ACCC2042 | AS2. 1 |
| AS2. 4 | AS2. 11 | AS2. 14 | AS2. 16 | AS2. 56 |
| AS2. 69 | AS2. 70 | AS2. 93 | AS2. 98 | AS2. 101 |
| AS2. 109 | AS2. 110 | AS2. 112 | AS2. 139 | AS2. 173 |
| AS2. 174 | AS2. 182 | AS2. 196 | AS2. 242 | AS2. 336 |
| AS2. 346 | AS2. 369 | AS2. 374 | AS2. 375 | AS2. 379 |
| AS2. 380 | AS2. 382 | AS2. 390 | AS2. 393 | AS2. 395 |
| AS2. 396 | AS2. 397 | AS2. 398 | AS2. 399 | AS2. 400 |
| AS2. 406 | AS2. 408 | AS2. 409 | AS2. 413 | AS2. 414 |
| AS2. 415 | AS2. 416 | AS2. 422 | AS2. 423 | AS2. 430 |
| AS2. 431 | AS2. 432 | AS2. 451 | AS2. 452 | AS2. 453 |
| AS2. 458 | AS2. 460 | AS2. 463 | AS2. 467 | AS2. 486 |
| AS2. 501 | AS2. 502 | AS2. 503 | AS2. 504 | AS2. 516 |
| AS2. 535 | AS2. 536 | AS2. 558 | AS2. 560 | AS2. 561 |
| AS2. 562 | AS2. 576 | AS2. 593 | AS2. 594 | AS2. 614 |
| AS2. 620 | AS2. 628 | AS2. 631 | AS2. 666 | AS2. 982 |
| AS2. 1190 | AS2. 1364 | AS2. 1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen
Var. *ellipsoideus* (Hansen) Dekker

| | | | | |
|---|---|---|---|---|
| ACCC2043 | AS2.2 | AS2.3 | AS2.8 | AS2.53 |
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

| | |
|---|---|
| AS2.131 | AS2.213 |

*Saccharomyces delbrueckii*

AS2.285

*Saccharomyces delbrueckii* Lindner ver.
*mongolicus* (Saito) Lodder et van Rij

| | |
|---|---|
| AS2.209 | AS2.1157 |

*Saccharomyces exiguous* Hansen

| | |
|---|---|
| AS2.349 | AS2.1158 |

*Saccharomyces fermentati*
(Saito) Lodder et van Rij

| | |
|---|---|
| AS2.286 | AS2.343 |

*Saccharomyces logos* van laer et Denamur ex Jorgensen

| | | |
|---|---|---|
| AS2.156 | AS2.327 | AS2.335 |

*Saccharomyces mellis* (Fabian et Quinet) Lodder et kreger van Rij

AS2.195

*Saccharomyces mellis* Microellipsoides Osterwalder

AS2.699

TABLE 1-continued

Exemplary Yeast Strains

*Saccharomyces oviformis* Osteralder

AS2.100

*Saccharomyces rosei* (Guilliermond) Lodder et Kreger van Rij

AS2.287

*Saccharomyces rouxii* Boutroux

| AS2.178 | AS2.180 | AS2.370 | AS2.371 |

*Saccharomyces sake* Yabe

ACCC2045

*Candida arborea*

AS2.566

*Candida lambica* (Lindner et Genoud) van. Uden et Buckley

AS2.1182

*Candida krusei* (Castellani) Berkhout

AS2.1045

*Candida lipolytica* (Harrison) Diddens et Lodder

| AS2.1207 | AS2.1216 | AS2.1220 | AS2.1379 | AS2.1398 |
| AS2.1399 | AS2.1400 | | | |

*Candida parapsilosis* (Ashford) Langeron et Talice Var. *intermedia* Van Rij et Verona

AS2.491

*Candida parapsilosis* (Ashford) Langeron et Talice

AS2.590

*Candida pulcherrima* (Lindner) Windisch

AS2.492

*Candida rugousa* (Anderson) Diddens et Lodder

| AS2.511 | AS2.1367 | AS2.1369 | AS2.1372 | AS2.1373 |
| AS2.1377 | AS2.1378 | AS2.1384 | | |

*Candida tropicalis* (Castellani) Berkhout

| ACCC2004 | ACCC2005 | ACCC2006 | AS2.164 | AS2.402 |
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

| AS2.120 | AS2.281 | AS2.1180 |

*Crebrothecium ashbyii* (Guilliermond) Routein (*Eremothecium ashbyii* Guilliermond)

| AS2.481 | AS2.482 | AS2.1197 |

*Geotrichum candidum* Link

| ACCC2016 | AS2.361 | AS2.498 | AS2.616 | AS2.1035 |
| AS2.1062 | AS2.1080 | AS2.1132 | AS2.1175 | AS2.1183 |

*Hansenula anomala* (Hansen)H et P sydow

| ACCC2018 | AS2.294 | AS2.295 | AS2.296 | AS2.297 |
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

*Hansenula arabitolgens* Fang

AS2.887

*Hansenula jadinii* (A. et R Sartory Weill et Meyer) Wickerham

ACCC2019

*Hansenula saturnus* (Klocker) H et P sydow

ACCC2020

*Hansenula schneggii* (Weber) Dekker

AS2.304

*Hansenula subpelliculosa* Bedford

| AS2.740 | AS2.760 | AS2.761 | AS2.770 | AS2.783 |
| AS2.790 | AS2.798 | AS2.866 | | |

*Kloeckera apiculata* (Reess emend. Klocker) Janke

| ACCC2022 | ACCC2023 | AS2.197 | AS2.496 | AS2.714 |
| ACCC2021 | AS2.711 | | | |

*Lipomycess starkeyi* Lodder et van Rij

| AS2.1390 | ACCC2024 |

*Pichia farinosa* (Lindner) Hansen

| ACCC2025 | ACCC2026 | AS2.86 | AS2.87 | AS2.705 |
| AS2.803 | | | | |

*Pichia membranaefaciens* Hansen

| ACCC2027 | AS2.89 | AS2.661 | AS2.1039 |

*Rhodosporidium toruloides* Banno

ACCC2028

*Rhodotorula glutinis* (Fresenius) Harrison

| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

*Rhodotorula aurantiaca* (Saito) Lodder

| AS2.102 | AS2.107 | AS2.278 | AS2.499 | AS2.694 |
| AS2.703 | AS2.704 | AS2.1146 | | |

*Saccharomyces carlsbergensis* Hansen

| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| IFFI1023 | IFFI1032 | IFFI1036 | IFFI1044 | IFFI1072 |
| IFFI1205 | IFFI1207 | | | |

*Saccharomyces willianus* Saccardo

| AS2.5 | AS2.7 | AS2.119 | AS2.152 | AS2.293 |
| AS2.381 | AS2.392 | AS2.434 | AS2.614 | AS2.1189 |

*Saccharomyces* sp.

AS2.311

*Saccharomycodes ludwigii* Hansen

| ACCC2044 | AS2.243 | AS2.508 |

*Saccharomycodes sinenses* Yue

AS2.1395

*Schizosaccharomyces octosporus* Beijerinck

| ACCC2046 | AS2.1148 |

*Schizosaccharomyces pombe* Lindner

| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |

*Sporobolomyces roseus* Kluyver et van Niel

| ACCC2049 | ACCC2050 | AS2.19 | AS2.962 | AS2.1036 |
| ACCC2051 | AS2.261 | AS2.262 | | |

TABLE 1-continued

Exemplary Yeast Strains

*Torulopsis candida* (Saito) Lodder

| AS2.270 | ACCC2052 | | |
| --- | --- | --- | --- |
| | *Torulopsis famta* (Harrison) Lodder et van Rij | | |
| ACCC2053 | AS2.685 | | |
| | *Torulopsis globosa* (Olson et Hammer) Lodder et van Rij | | |
| ACCC2054 | AS2.202 | | |
| | *Torulopsis inconspicua* Lodder et Kreger van Rij | | |
| AS2.75 | | | |
| | *Trichosporon behrendii* Lodder et Kreger van Rij | | |
| ACCC2056 | AS2.1193 | | |
| | *Trichosporon capitatum* Diddens et Lodder | | |
| ACCC2056 | AS2.1385 | | |
| | *Trichosporon cutaneum* (de Beurm et al.) Ota | | |
| ACCC2057 | AS2.25 | AS2.570 | AS2.571 AS2.1374 |
| | *Wickerhamia fluorescens* (Soneda) Soneda | | |
| ACCC2058 | AS2.1388 | | |

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 18000 MHz to 18200 MHz. Exemplary frequencies include 18108, 18114, 18121, 18126, and 18130 MHz. The field strength of the electric field useful in this invention ranges from about 150 to 500 mV/cm (e.g., 220–240, 340–360, 320–360, 310–350, 390–420, or 330–350 mV/cm). Exemplary field strengths include 122, 126, 220, 232, 235, 244, 322, 342, 345, 347, 352, and 405 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of 2, 3, 4, 5, 6, 7, 8, 9 or 10 EMFs in a series.

Although the yeast cells can be activated after even a few hours of culturing in the presence of an EMF, it may be preferred that the activated yeast cells be allowed to multiply and grow in the presence of the EMF(s) for a total of 16–120 hours (e.g., 60 to 98 hours).

FIG. 1 illustrates an exemplary apparatus for generating alternating electric fields. An electric field of a desired frequency and intensity can be generated by an AC source (3) capable of generating an alternating electric field, preferably in a sinusoidal wave form, in the frequency range of 5 to 20,000 MHz. Signal generators capable of generating signals with a narrower frequency range can also be used. If desired, a signal amplifier can also be used to increase the output. The culture container (2) can be made from a non-conductive material, e.g., glass, plastic or ceramic. The cable connecting the culture container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm, and 25–30 cm from the bottom of the container (2), respectively. The number of metal wires/tubes used can be from 1 to 10 (e.g., 2 to 3). It is recommended, though not mandated, that for a culture having a volume up to 10 L, metal wires/tubes having a diameter of 0.5 to 2 mm be used. For a culture having a volume of 10–100 L, metal wires/tubes having a diameter of 3 to 5 mm can be used. For a culture having a volume of 100–1000 L, metal wires/tubes having a diameter of 6 to 15 mm can be used. For a culture having a volume greater than 1000 L, metal wires/tubes having a diameter of 20–25 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy.

III. Culture Media

Culture media useful in this invention contain sources of nutrients that can be assimilated by yeast cells. Complex carbon-containing substances in a suitable form (e.g., carbohydrates such as sucrose, glucose, dextrose, maltose, xylose, cellulose, starch, etc.) can be the carbon sources for yeast cells. The exact quantity of the carbon sources can be adjusted in accordance with the other ingredients of the medium. In general, the amount of carbohydrate varies between about 1% and 10% by weight of the medium and preferably between about 1% and 5%, and most preferably about 2%. These carbon sources can be used individually or in combination. Amino acid-containing substances such as beef extract and peptone can also be added. In general, the amount of amino acid containing substances varies between about 0.1% and 1% by weight of the medium and preferably between about 0.1% and 0.5%. Among the inorganic salts which can be added to a culture medium are the customary salts capable of yielding sodium, potassium, calcium, phosphate, sulfate, carbonate, and like ions. Non-limiting examples of nutrient inorganic salts are $(NH_4)_2HPO_4$, $CaCO_3$, $KH_2PO_4$, $K_2 HPO_4$, $MgSO_4$, NaCl, and $CaSO_4$.

IV. Electromagnetic Activation of Yeast Cells

To activate or enhance the ability of yeast cells to produce agents beneficial for the gastrointestinal system, these cells can be cultured in an appropriate medium under sterile conditions at 20–35° C. (e.g., 28–32° C.) for a sufficient amount of time (e.g., 60–98 hours) in an alternating electric field or a series of alternating electric fields as described above.

An exemplary set-up of the culture process is depicted in FIG. 1 (see above). An exemplary culture medium contains the following per 1000 ml of sterile water: 20 g of sucrose, 40 μg of Vitamin B1 (sterilized before use), 50 μg of Vitamin B6 (sterilized before use), 30 μg of Vitamin B12, 0.2 g of $KH_2PO_4$, 0.2 g of $MgSO_4.7H_2O$, 0.25 g of NaCl, 0.1 g of $CaSO_4.2H_2O$, 3 g of $CaCO_3.5H_2O$, and 2.5 g of yeast extract. Yeast cells of the desired strain(s) are then added to the culture medium to form a mixture containing $1 \times 10^8$ cells per 1000 ml of culture medium. The yeast cells can be of any of the strains listed in Table 1. The mixture is then added to the apparatus shown in FIG. 1.

The activation process of the yeast cells involves the following steps: (1) maintaining the temperature of the activation apparatus at 24–33° C. (e.g., 28–32° C.), and culturing the yeast cells for 25–33 hours (e.g., 32 hours); (2) applying an alternating electric field having a frequency of 18108 MHz and a field strength of 220–240 mV/cm (e.g., 231–233 mV/cm) for 16–22 hours (e.g., 20 hours); (3) then applying an alternating electric field having a frequency of 18114 MHz and a field strength of 220–240 mV/cm (e.g., 234–236 mV/cm) for 22–28 hours (e.g., 20 hours); (4) then applying an alternating electric field having a frequency of 18121 MHz and a field strength of 340–360 mV/cm (e.g., 350–354 mV/cm) for 22–28 hours (e.g., 26 hours); (5) then applying an alternating electric field having a frequency of 18126 MHz and a field strength of 320–360 mV/cm (e.g., 343–347 mV/cm) for 12–18 hours (e.g., 16 hours); and (6) then applying an alternating electric field having a frequency of 18130 MHz and a field strength of 310–350 mV/cm (e.g., 320–324 mV/cm) for 15–20 hours (e.g., 18 hours). The activated yeast cells are then recovered from the culture medium by various methods known in the art, dried (e.g., by lyophilization) and stored at 4° C. Preferably, the concentration of the dried yeast cells are no less than $10^{10}$ cells/g.

V. Acclimatization of Yeast Cells To the Gastric Environment

Because the yeast compositions of this invention must pass through the stomach before reaching the small intestine, where the effective components are released from these yeast cells, it is preferred that these yeast cells be cultured under acidic conditions to acclimatize the cells to the gastric juice. This acclimatization process results in better viability of the yeast cells in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture is then cultured first in the presence of an alternating electric field having a frequency of 18226 MHz and a field strength of 390–420 mV/cm (e.g., 403–407 mV/cm) at about 28 to 32° C. for 25 to 48 hours (e.g., 46 hours). The resultant yeast cells can then be further incubated in the presence of an alternating electric field having a frequency of 18130 MHz and a field strength of 330–350 mV/cm (e.g., 340–344 mV/cm) at about 28 to 32° C. for 20 to 40 hours (e.g., 28 hours). The resulting acclimatized yeast cells are then either dried and stored in powder form ($\leq 10^{10}$ cells/g) at room temperature or in vacuum at 0–4° C.

An exemplary acclimatizing culture medium is made by mixing 700 ml fresh pig gastric juice and 300 ml wild Chinese hawthorn extract. The pH of the acclimatizing culture medium is adjusted to 2.5 with 0.1 M hydrochloric acid (HCl) and/or 0.2 M potassium biphthalate ($C_6H_4$(COOK)COOH). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. The supernatant is collected for use in the acclimatizing culture medium. To prepare the wild Chinese hawthorn extract, 500 g of fresh wild Chinese hawthorn is dried under sterile conditions to reduce water content ($\leq 8\%$). The dried fruit is then ground ($\geq 20$ mesh) and added to 1500 ml of sterile water. The hawthorn slurry is allowed to stand for 6 hours at 4° C. under sterile conditions. The hawthorn supernatant is collected to be used in the acclimatizing culture medium.

VI. Manufacture of Yeast Compositions

Figure 2:
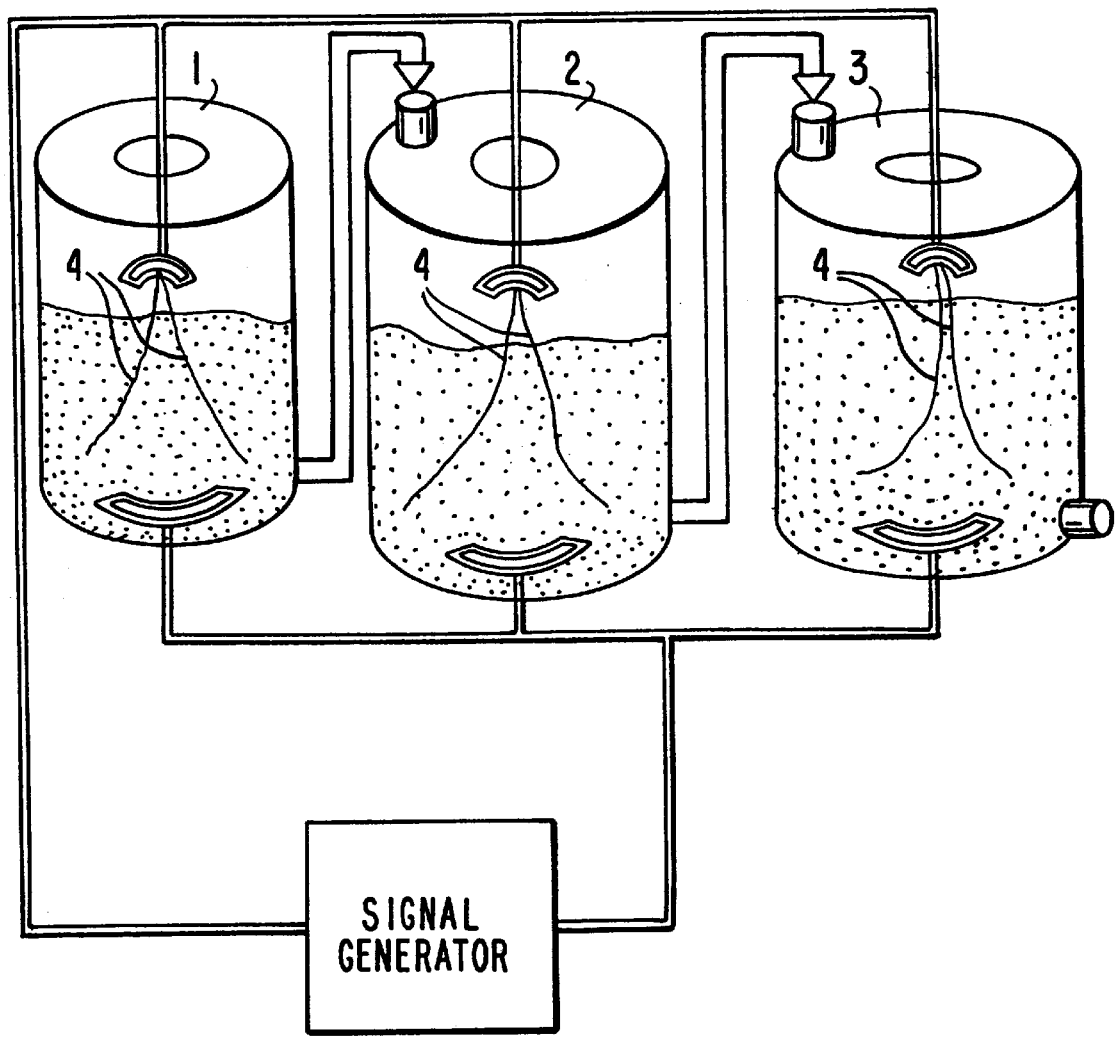
FIG. 2 is a schematic diagram showing an exemplary apparatus for making yeast compositions of the invention. The apparatus comprises a signal generator and interconnected containers 1, 2 and 3.

To manufacture the yeast compositions of the invention, an apparatus depicted in FIG. 2 or an equivalent thereof can be used. This apparatus includes three containers, a first container (1), a second container (2), and a third container (3), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of Wu Wei Zi (*Schisandra chinensis* (Turez) Baill seeds) extract, and 100 L of soy bean extract. To prepare hawthorn, jujube and Wu Wei Zi extracts, the fresh fruits are washed and dried under sterile conditions to reduce the water content to no higher than 8%. One hundred kilograms of the dried fruits are then ground ($\geq 20$ mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and centrifuged at 1000 rpm to remove insoluble residues. To make the culture medium, these ingredients are mixed according to the above recipe, and the mixture is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (1) shown in FIG. 2. The yeast cells are then cultured in the presence of an alternating electric field having a frequency of 18126 MHz and a field strength of about 330–360 mV/cm (e.g., 345–349 mV/cm) at 28–32° C. under sterile conditions for 18 hours. The yeast cells are further incubated in an alternating electric field having a frequency of 18130 MHz and a field strength of 310–330 mV/cm (e.g., 320–324 mV/cm). The culturing continues for another 12 hours.

The yeast culture is then transferred from the first container (1) to the second container (2) which contains 1000 L of culture medium (if need be, a new batch of yeast culture can be started in the now available first container (1)), and subjected to an alternating electric field having a frequency of 18126 MHz and a field strength of 220–250 mV/cm (e.g., 244 mV/cm) for ten hours. Subsequently the frequency and field strength of the electric field are changed to 18,130 MHz and 210–240 mV/cm (e.g., 218–222 mV/cm), respectively. The culturing continues for another ten hours.

The yeast culture is then transferred from the second container (2) to the third container (3) which contains 1000 L of culture medium, and subjected to an alternating electric field having a frequency of 18126 MHz and a field strength of 110–130 mV/cm (e.g., 124–128 mV/cm) for fifteen hours. Subsequently the frequency and field strength of the electric field are changed to 18130 MHz and 110–140 mV/cm (e.g., 120–124 mV/cm), respectively. The culturing continues for another ten hours.

The yeast culture from the third container (3) can then be packaged into vacuum sealed bottles for use as dietary supplement, e.g., health drinks. If desired, the final yeast culture can also be dried within 24 hours and stored in powder form. The dietary supplement can be taken three to four times daily at 30–60 ml per dose for a three-month period, preferably 10–30 minutes before meals and at bedtime.

In some embodiments, the compositions of the invention can also be administered intravenously or peritoneally in the form of a sterile injectable preparation. Such a sterile preparation can be prepared as follows. A sterilized health drink composition is first treated under ultrasound (1000 Hz) for 10 minutes and then centrifuged at 4355 g for another 10 minutes. The resulting supernatant is adjusted to pH 7.2–7.4 using 1 M NaOH and subsequently filtered through a membrane (0.22 $\mu$m for intravenous injection and 0.45 $\mu$m for peritoneal injection) under sterile conditions. The resulting sterile preparation is submerged in a 35–38° C. water bath for 30 minutes before use.

The yeast compositions of the present invention are derived from yeasts used in food and pharmaceutical industries. The yeast compositions are thus devoid of side effects associated with many pharmaceutical compounds.

VII. EXAMPLES

The following examples are meant to illustrate the methods and materials of the present invention. Suitable modifications and adaptations of the described conditions and parameters which are obvious to those skilled in the art are within the spirit and scope of the present invention.

The activated yeast compositions used in the following experiments were prepared as described above, using *Saccharomyces cerevisiae* Hansen AS2.558 cells cultured in the presence of an alternating electric field having the electric field frequency and field strength exemplified in the parentheses following the recommended ranges listed in Section IV, supra. Control yeast compositions were those prepared in the same manner except that the yeast cells were cultured in the absence of EMFs. Unless otherwise indicated, the yeast compositions and the corresponding controls were administered to the animals by intragastric feeding.

Example 1

Secretion of Gastric Acid and Pepsin

The activated yeast composition was shown to modulate the secretion of gastric acid and pepsin in the stomach of rats. This result was obtained as follows.

Thirty Wistar rats (8–10 months old) were divided into three groups, each having ten rats. Rats in group A were administered 3 ml of the activated yeast composition once daily for three days. Rats in groups B anc C were given the control yeast composition and saline, respectively. The rats in all three groups were otherwise maintained under the same conditions.

After the third dose of yeast composition was administered to the animals, the animals were given only water, no food, for the next 24 hours. The rats were then anesthetized with ether. An incision was then made in the middle of the abdomen of the animal and the stomach was taken out gently. The pylorus was then ligated. The activated yeast composition, control yeast composition, and saline were administered to the animals, at 3 ml/rat daily, through the duodenum by injection. The stomach was replaced in the abdomen and the incision was stitched back. Two hours later, the abdomen was re-opened and the stomach was taken out. The cardia was ligated and the whole stomach was removed from the animal. The stomach was cut open along the greater curvature, and gastric contents were collected into a conical centrifuge tube, measured for its pH value, and centrifuged at 1500 rpm for 10 minutes. The supernatant was collected.

The pH of the supernatant was measured by acid-base titration. To do this, one drop of phenolphthalein was added to 1 ml of the supernatant, and then 10 mM NaOH was added to the supernatant until neutralization occurred, as indicated by the color of phenolphthalein. The gastric acid concentration (M) was equal in value to the volume (ml) of the consumed NaOH solution. The amount of gastric acid secretion per hour by the animal (mmol/hour) was equal to

[gastric acid concentration (M)].[volume of gastric juice (ml/hour)]/2

The pepsin concentration in the gastric juice was determined by the Anson method. To do this, the gastric juice was diluted 1:50 with 0.04 M HCl at 37° C. Then 2 ml of hemoglobin substrate solution (infra) was added to 0.5 ml of the diluent and incubated in a 37° C. water bath for exactly 10 minutes. Next, 5 ml of 5% trichloroacetic acid was added and the sample was incubated at room temperature for 30 minutes. The sample was then centrifuged and the supernatant was collected. Five ml of 0.5 M $Na_2CO_3$ and 0.5 ml of phenolphthalein were added to 1 ml of the supernatant and mixed quickly. The mixture was incubated at room temperature for 1 hour. The control reaction was performed in the same manner, except that the 2 ml hemoglobin substrate solution was added immediately after, rather than before, the 37° C. water bath incubation step. The hemoglobin substrate solution was made as follows: 2.5 g of purified hemoglobin (powder) was dissolved in 100 ml of a diluted merthiolate solution (which was made by mixing 2.5 ml of 0.1% merthiolate solution with distilled $H_2O$ to bring the volume to 100 ml). The solution was then centrifuged, and the supernatant was taken and stored at 4° C. Immediately before use, the 2.5% hemoglobin stock solution was mixed with 0.3 M HCL (4:1 v/v).

Optical densities of the samples were then measured at 640 nm, using a spectrophotometer calibrated with distilled water. Pepsin activities in the samples were calculated based on an L-Tyrosine standard curve. To make an L-Tyrosine standard curve, L-Tyrosine was diluted at various concentrations, and $Na_2CO_3$ and phenolphthalein were added and optical densities were measured, all as described above.

The experimental results are summarized in Table 2 below.

TABLE 2

| Group | Number of animals | Gastric juice vol. (ml) | Acid concentration (mM) | Acid secretion rate (mmol/h) | Pepsin activity (µg/ml/min) |
|---|---|---|---|---|---|
| A | 10 | 7.86 ± 0.5 | 18.8 ± 1.6 | 48.89 ± 1.6 | 3.63 ± 0.2 |
| B | 10 | 4.01 ± 0.7 | 10.2 ± 1.3 | 20.12 ± 1.8 | 1.81 ± 0.1 |
| C | 10 | 3.92 ± 0.8 | 9.6 ± 1.2 | 19.58 ± 3.6 | 1.79 ± 0.1 |

These data demonstrate that the activated yeast composition notably increased the secretion of gastric acid and the activity level of pepsin, as compared to the control yeast composition and saline.

Example 2

Inhibition of Gastric Ulcer Induced by Stress

Thirty Wistar rats (10–12 months old; 150–180 g in weight) were divided into three equal groups. The animals were given no food but water for 24 hours. Then rats in group A were each given daily 3 ml of the activated yeast composition for 13 consecutive days. Rats in groups B and C were given the same volume of the control composition and saline, respectively, in lieu of the activated yeast composition.

On the fourteenth day, each rat was lightly anesthetized with ether, laid on its back on a steel board specifically made for rat dissection, and fastened to the steel board. The rat and the steel board were wrapped around with soft metal mesh, the metal wrap fastened in place with threads. The activated yeast composition and the controls were then administered to the rats. Thirty minutes later, the rat, together with the steel board, was placed vertically in a 23° C. water bath, with the ensisternum just above the water. Twenty hours later, the rat underwent bloodletting and was sacrificed. The abdomen was opened. After the pylorus and cardia were ligated, the stomach was retrieved. The stomach was injected with 6 ml of saline from the gastric gland and fixed in 1% (v/v) formaldehyde for ten minutes. The stomach was then opened by an incision along the greater curvature. The interior of the stomach was examined for signs of ulcer.

Stress-induced gastric ulcer is characterized by lesions along the blood vessels in the gastric gland, which are typically covered with coagulated blood. When the coagulated blood is removed, dark brown ulcerous rugae can be revealed. The total length of the ulcerous rugae is an indicator of the severity of gastric ulcer.

In this experiment, the ulcer-preventing activity of the yeast composition was calculated as follows: Ulcer-preventing activity (%)=(total ulcer length of group B rat–total ulcer length of group A rat)/total ulcer length of group B rat.

The results are shown in Table 3 below.

TABLE 3

| Group | Number of animal | length of ulcerous rugae (mm) | percentage inhibition |
|---|---|---|---|
| A | 10 | 2.13 ± 0.06 | 96.2 |
| B | 10 | 54.63 ± 2.32 | 3.4 |
| C | 10 | 56.57 ± 11.22 | 0 |

These data demonstrate that the activated yeast composition significantly reduced the incidence and severity of gastric ulcer induced by stress, as compared to the control yeast composition and saline.

Example 3

Inhibition of Gastric Ulcer Induced by *Campylobactor plori*

*Campylobactor plori* has been shown to be one cause of gastric ulcer. It is known that the presence of urease in the mucosal membrane of gastric antrum has a 91.2% correlation rate with the presence of *C. plori* in the membrane.

Ninety Wistar rats (six months old) were divided into groups A–E, each having 20 rats except group D, which had 10. Rats in group A were given 2 ml of 60% ethanol per animal once every five days for a month. In the second month, the ethanol was given once every seven days. During this two-month period, the rats' drinking water contained 20 mM sodium deoxycholate. From the beginning of the third month to the end of the sixth month, the 60% ethanol treatment was discontinued. Instead, the rats' drinking water contained 20 mM sodium deoxycholate and 30% ethanol. This drinking solution was replaced every seven days. During the entire six-month period, the rats were given daily 2 ml of the activated yeast composition per animal.

Rats in groups B and C were treated in the same manner as in group A, except that the rats were given the control yeast composition and saline, respectively, instead of the activated yeast composition.

Rats in group D were given no treatment except that they were given 2 ml of saline daily for six months.

Rats in group E were treated in the manner as rats in group C, except that for the former group, regular water was provided for drinking after the first two months.

At the end of the sixth month, the animals were sacrificed, and their stomachs were retrieved as described above for further analysis.

1. Urease Assay

Under sterile conditions, a piece of gastric antrum tissue (0.2×10 $mm^2$) was placed in a urease reaction petri dish and incubated at 37° C. for 24 hours. The presence of a pink ring indicated the activity of urease. The time for the entire culture dish to turn pink was recorded.

2. Morphological Analysis

The gastric antrum mucosal membrane was sectioned, dried at room temperature and stained with 1% Fuchin basic. The sections were then examined under oil microscope.

3. Histological Analysis

A section of the stomach along the lesser curvature spanning from the proventriculus to the pylorus was obtained and fixed in a 10% formaldehyde solution, embedded in paraffin and sectioned. The sections were stained with HE (hematoxylin and eosin) and examined under light microscope. Sections deemed typical of the condition of the stomach were stained with Periodic acid-Schiff Alcian blue and Van Gieson for further histological studies, using the China National Standard for Chronic Gastritis (Zhang Jun-Tian, Ed., Experimental Methods in Modern Pharmacology, Octorber 1998, Union Medical University Publishing House, Beijing, China) as guidance. The inflammatory conditions and the thickness of the mucous layer and muscular layer of mucosa were examined using semi-quantitative methods.

The whole layer of gastric mucosa was examined under lower power microscope. Each section was observed for 10 visual fields, including 4 for antrum, 1 for juncture of gastric antrum, 1 for juncture of proventriculus and gastric glands, 4 for body of stomach. The severity of inflammation was indicated by 4 levels: namely "−" for negative in inflammation, "+" for a few inflammatory cells spread on the superficial layer of gastric mucosa and fundus of stomach, "++" for a number of inflammatory cells found in every layer of gastric mucosa, "+++" for infiltration of significant number of inflammatory cells accumulated inside the gastric mucosa. Given the levels of inflamation, the average values of the 4 parts: antrum, juncture of gastric antrum, body of stomach, and juncture of proventruiculus and stomach glands were compared. The thicknesses of the mucous layer and the muscular layer of the stomach were measured in mm with micrometer. Each section was examined with 10 fields of vision–5 for antrum and 5 for fundus. The connective tissue proliferation was indicated by comparing the average values of antrum and fundus.

The data from these experiments are shown in Table 4 below.

TABLE 4

| Group | Number of animals | Degree of gastritis | | urease reaction | |
|---|---|---|---|---|---|
| | | Body of Stomach (Somatic part) (mm) | Antrum (mm) | + | − |
| A | 20 | 0.37 ± 0.24 | 0.81 ± 0.22 | 2 | 18 |
| B | 20 | 1.0 ± 0.47 | 1.49 ± 0.84 | 11 | 9 |
| C | 20 | 1.3 ± 0.82 | 1.55 ± 0.85 | 9 | 11 |
| D | 10 | 0.34 ± 0.23 | 0.77 ± 0.87 | 2 | 8 |
| E | 20 | 1.1 ± 0.55 | 1.59 ± 0.57 | 11 | 9 |

These data demonstrate that the activated yeast composition significantly alleviated gastric ulcer caused by *Campylobacter plori*, as compared to the control yeast composition and saline.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by their ability to alleviate gastric ulcer in a mammal, said ability resulting from their having been cultured in the presence of an alternating electric field having a frequency in the range of 18100 to 18150 MHz and a field strength in the range of 100 to 420 mV/cm, as compared to yeast cells not having been so cultured.

2. The composition of claim 1, wherein said frequency is in the range of 18108 to 18130 MHz.

3. The composition of claim 1, wherein said field strength is in the range of 120 to 410 mV/cm.

4. The composition of claim 1, wherein said yeast cells are of the species selected from the group consisting of *Saccharomyces cerevisiae, Saccharomyces carlsbergensis, Saccharomyces chevalieri, Saccharomyces delbrueckii, Saccharomyces exiguous, Saccharomyces fermentati, Saccharomyces logos, Saccharomyces mellis, Saccharomyces oviformis, Saccharomyces rosei, Saccharomyces rouxii, Saccharomyces sake, Saccharomyces uvarum, Saccharomyces willianus,* Saccharomyces sp., *Schizosaccharomyces octosporus, Schizosaccharomyces pombe, Sporobolomyces roseus, Torulopsis candida, Torulopsis famta, Torulopsis globosa, Torulopsis inconspicua, Trichosporon behrendii, Trichosporon capitatum, Trichosporon cutaneum, Wickerhamia fluoresens, Candida arborea, Candida krusei, Candida lambica, Candida lipolytica, Candida parapsilosis, Candida pulcherrima, Candida rugousa, Candida tropicalis, Candida utilis, Crebrothecium ashbyii, Geotrichum candidum, Hansenula anomala, Hansenula arabitolgens, Hansenula jadinii, Hansenula saturnus, Hansenula schneggi, Hansenula subpelliculosa, Kloeckera apicuiata, Lipomyces starkeyi, Pichiafarinosa, Pichia membranaefaciens, Rhodosporidium toruloides, Rhodotorula glutinis, Rhodotorula minuta, Rhodotorula rubar, Rhodotorula aurantiaca, Saccharomycodes ludwigii,* and *Saccharomycodes sinenses.*

5. The composition of claim 1, wherein said yeast cells are of the strain deposited at the China General Microbiological Culture Collection Center with an accession number selected from the group consisting of *Saccharomyces cerevisiae* Hansen AS2.375, AS2.501, AS2.502, AS2.503, AS2.504, AS2.535, AS2.558, AS2.560, AS2.561, AS2.562 and IFFI1048, and *Saccharomyces carlsbergensis* Hansen AS2.420 and AS2.444.

6. The composition of claim 1, wherein said composition is in the form of a tablet, powder, or a health drink.

7. The composition of claim 1, wherein said composition is in the form of a health drink.

8. A method of treating gastric discomfort in a subject, comprising introducing orally the composition of claim 1 to the subject.

9. A method of preparing a yeast composition, comprising culturing a plurality of yeast cells in the presence of an alternating electric field having a frequency in the range of 18100 to 18150 MHz and a field strength in the range of 100 to 420 mV/cm for a period of time sufficient to substantially increase the capability of said plurality of yeast cells to increase secretion of gastric juice and alleviate gastric ulcer in a mammal, as compared to yeast cells not having been so cultured.

* * * * *